United States Patent [19]

Garcés

[11] Patent Number: 4,499,320

[45] Date of Patent: Feb. 12, 1985

[54] ALKYLATION PROCESS EMPLOYING MAGNESIUM SILICATE COMPOSITIONS

[75] Inventor: Juan M. Garcés, Midland, Mich.

[73] Assignee: The Dow Chemical Company, Midland, Mich.

[21] Appl. No.: 484,112

[22] Filed: Apr. 11, 1983

Related U.S. Application Data

[63] Continuation-in-part of Ser. No. 327,870, Dec. 7, 1981.

[51] Int. Cl.³ ............................................. C07C 2/68
[52] U.S. Cl. .................................................... 585/467
[58] Field of Search ........................................ 585/467

[56] References Cited

U.S. PATENT DOCUMENTS

| | | | |
|---|---|---|---|
| 3,893,910 | 7/1975 | Robson | 208/138 |
| 4,128,592 | 12/1978 | Kaeding | 585/467 |
| 4,158,024 | 6/1979 | Kaeding et al. | 585/467 |
| 4,205,189 | 5/1980 | Young et al. | 585/467 |

*Primary Examiner*—Curtis R. Davis

[57] ABSTRACT

Alkylation of aromatic compounds employing novel crystalline porous magnesium silicates having catalytic activity.

27 Claims, 3 Drawing Figures

ALKYLATION PROCESS EMPLOYING MAGNESIUM SILICATE COMPOSITIONS

CROSS-REFERENCE TO RELATED APPLICATION

This a continuation-in-part of co-pending application Ser. No. 327,870, filed Dec. 7, 1981.

BACKGROUND OF THE INVENTION

The present invention relates to the alkylation of aromatic compounds by the use of novel magnesium silicates. In particular, the present invention relates to the alkylation of benzene and alkylbenzenes or mixtures thereof by the use of novel magnesium silicates having a porous structure and catalytic properties.

Processes for the alkylation of aromatic compounds and particularly, processes for the ethylation of toluene are well-known, see e.g., U.S. Pat. No. 4,086,287, and references cited therein. Catalysts for the reaction include those generally referred to as zeolites such as the ZSM-5 type zeolite catalysts and similar crystalline aluminosilicates such as those disclosed in the above U.S. Pat. No. 4,086,287.

While the above noted prior art is considered of interest in connection with the subject matter of the instant application, the alkylation process described herein employs previously unknown porous magnesium silicate catalysts. Advantageously, the present process employs wide extremes of temperature and reactant ratios, and has not, as far as is known, been heretobefore described.

SUMMARY OF THE INVENTION

The present invention is an alkylation process employing as a catalyst a novel porous crystalline magnesium silicate. The amount of magnesium present in this silicate may vary. However, for all compositions employed in the present invention, it is essential that some magnesium which is not ion-exchangeable by conventional techniques be present in the silicate. Conventional techniques of ion-exchange are presented in Breck, *Zeolite Molecular Sieves*, John Wiley & Sons (1974). Other elements may be present in these novel silicates as impurities such as aluminum, germanium, gallium, etc., or chemicals may be deliberately added either to modify or improve the properties of the magnesium silicate or for other advantageous reasons, for example, to ameliorate process parameters.

Many but not all of these novel silicates have a composition which may be expressed according to the following formula in terms of the molar ratios of oxides on a dry basis:

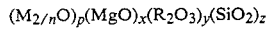

$(M_{2/n}O)_p(MgO)_x(R_2O_3)_y(SiO_2)_z$ wherein M is at least one ion-exchangeable cation having a valence of n; R is at least one element (with valence 3+) which is not ion-exchangeable by conventional means; $x/z > 0$; $y/z \geq 0$; $p/n > y$; and p, x, z are positive numbers and y is a positive number of zero. By dry basis is meant material which has been heated in air at about 500° C. for a period of one hour or more. The invention is not limited to the use of such dried material or said oxide forms, rather its composition may be presented in terms of oxides and on a dry basis (as in the above formula) in order to provide a means for identifying some of the novel compositions. Furthermore, compositions employed in the present invention may also incorporate one or more elements which are not ion-exchangeable and have a valence other than 3+. These additional elements if present may be substituted for silicon or located as members of the framework lattice structure. In the above-mentioned formula which accounts for some but not all compositions of the invention, element R need not be present. Other formulas may be written by those skilled in the art to identify particular subsets or embodiments of the present invention which comprises porous crystalline magnesium silicates.

As employed in the present alkylation process, the above compositions may be advantageously incorporated with binders or other materials which are well-known in the art. They may also be modified with one or more elements or compounds by deposition, occlusion, ion-exchange or other techniques known to those skilled in the art to enhance, supplement or alter the properties or usefulness of the composition. See, e.g., Breck, *Zeolite Molecular Sieves*, John Wiley & Sons (1974).

The above-described magnesium silicates are prepared by hydrothermal methods from a variety of silicate and magnesium sources leading to products employable in this invention, all of which incorporate magnesium into the structure of the resulting crystalline silicate.

The alkylation is performed by combining the aromatic compound with an alkylation agent in the presence of the magnesium silicate catalyst. The reaction is conducted at elevated temperatures and pressures.

DETAILED DESCRIPTION OF THE INVENTION

Figure 1:
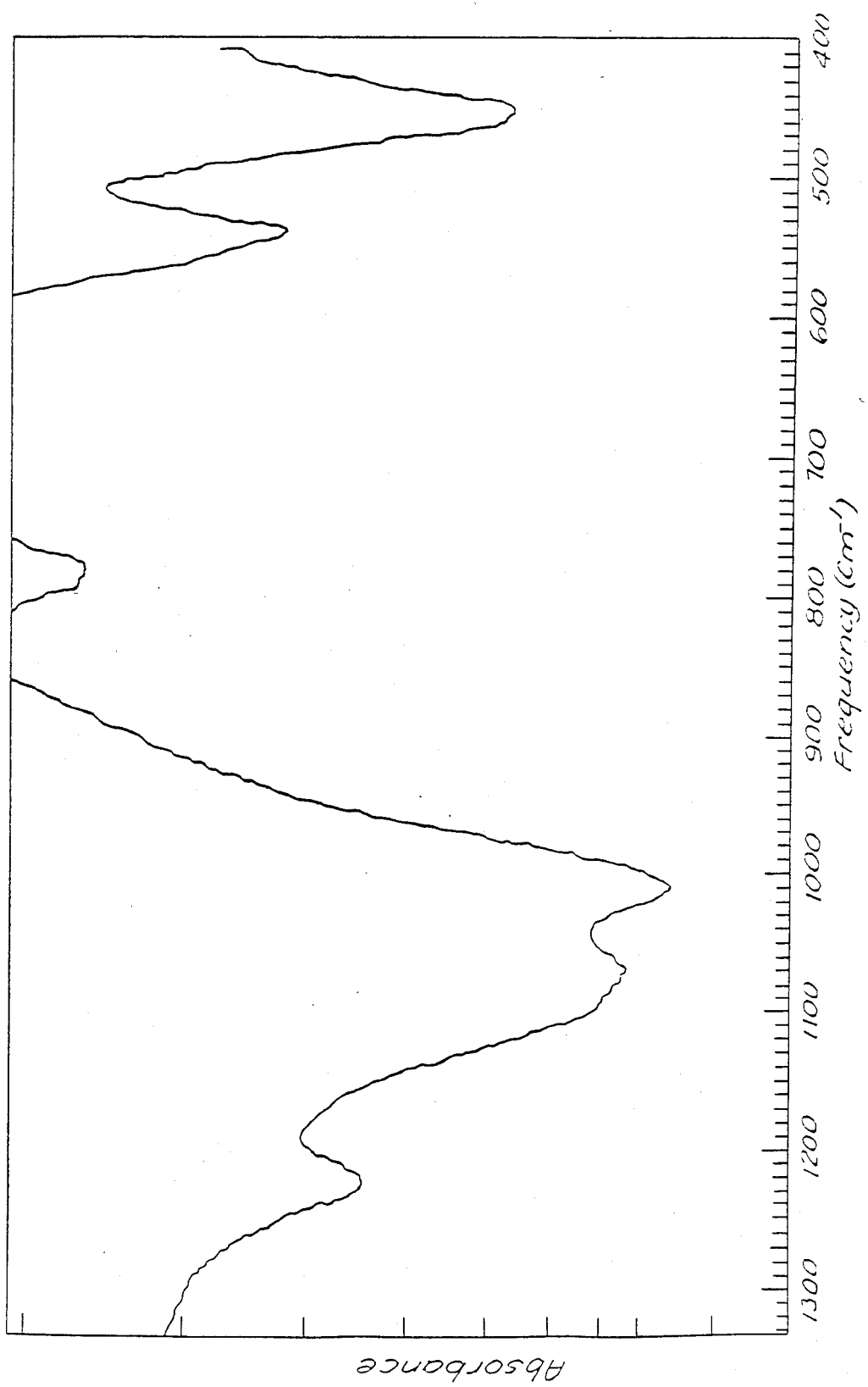
FIGS. 1, 2 and 3 illustrate the infra red patterns characteristic of the magnesium silicates described in this application.

The term crystalline when used in this document refers to materials which are recognized by those skilled in the art as having a highly ordered structure. Three dimensional periodicity is characteristic of a highly ordered structure. The skilled artisan recognizes that evidence of such periodicity may be presented by catalytic reactivity, infrared spectroscopy or other means of analysis as well as by the commonplace X-ray diffraction analysis. Magnesium silicates employed in the present invention are "crystalline" as that term is characterized above even if said silicates appear amorphous to X-ray diffraction analysis if a skilled artisan recognizes a highly ordered structure by other evidence. A recent article by P. A. Jacobs et al., "Evidence of X-ray Amorphous Zeolites", *J.C.S. Chem. Comm.*, 591, 1981, is hereby incorporated by reference in its entirety in this document.

By the term "porous" are meant those silicates having a framework structure containing cavities capable of allowing the entrance or absorbance of aromatic molecules.

Due to the differences in ionic radii of $Si^{IV}$ (0.41 Å) and $Al^{III}$ (0.50 Å) replacement of Si by Al in $TO_4$ sites will cause a unit cell volume expansion in most zeolites. The degree of unit cell volume expansion will depend on the amount of Al substitution for Si in the $TO_4$ sites. If the substitution is low, as in some ZSM-5 and silicalite zeolites, high resolution, calibrated X-ray diffraction techniques must be utilized to detect the expansion.

Similarly, in the magnesium silicates used in the present invention, it is believed that nonion-exchangeable Mg is contained in the zeolite lattice. Replacement of $Si^{IV}$ (0.41 Å) by $Mg^{II}$ (0.65 Å) in $TO_4$ sites will also cause a unit cell expansion. Once again, the amount of Mg substitution for Si, will influence the degree of cell volume expansion.

Evidencing element location in a framework lattice structure by determining cell volume expansion (construction) has been done by others skilled in making silicates. See, e.g., M. Taramasso, G. Perego and B. Notari, "Molecular Sieve Borosilicates", *Proceedings of the Fifth International Conference on Zeolites*, 40–48 at 44 (Heyden & Sons Ltd.) (1980).

High resolution X-ray powder diffraction data were obtained from Huber-Guinier powder diffraction cameras equipped with Ge and quartz monochromators for providing $CuK_{\alpha 1}$ and $FeK_{\alpha 1}$ radiation, respectively. The films were calibrated, with well-known internal standards such as NBS Si (NBS Circular 539, Vol. 9, p. 3) or $As_2O_3$, scanned with a densitometer and the resulting data profile fit by techniques described in: J. W. Edmonds and W. W. Henslee, *Adv. in X-ray Anal.*, 22, 143 (1978) and J. W. Edmonds, "Precision Guinier X-ray Powder Diffraction Data", NBS Special Publication 567, *Proceedings of Symposium on Accuracy in Powder Diffraction Held at NBS, Gaithersburg, MD*, June 11–15, 1979 (Issued February 1980) (the papers are hereby incorporated by reference). The calibrated data were least-squares refined and fitted to obtain accurate cell dimensions and volumes.

Using data from the method described above and using single crystal X-ray crystallographic data from the literature, the cell volume for the present invention where $Mg^{II}$ is believed to replace $Si^{IV}$, can be compared to the cell volume of silicalite which has $Si^{IV}$ in all the $TO_4$ sites. Typical data are shown in Table I, for either anhydrous zeolites or calcined zeolites. (Minimum calcination of 500° C. for 1 hour.)

TABLE I

| Compound | Cell Volumes Volume (Å³) | Reference |
| --- | --- | --- |
| Silicalite | 5306 | 1 |
| Silicalite | 5305 | 2 |
| Magnesium Silicate | 5347 | 2 |
| Magnesium Silicate | 5349 | 2 |

[1] Cell volumes were obtained from the lattice parameters given in an article by E. M. Flanigen, J. M. Bennett, R. W. Grose, J. P. Cohen, R. L. Patton, R. M. Kirchner and J. V. Smith, Nature, 271, 512 (1978).
[2] Cell volumes were calculated using the National Bureau of Standards - Geological Survey Lattice Parameter Refinement Program written by Dan Appleman (available through NTIS) on XRD data obtained on samples made either according to a process herein described or according to the silicalite patent, U.S. Pat. No. 4,061,724.

The above values are typical examples of cell volumes. The difference between these volumes shows a cell volume expansion. The exact amount of expansion will be composition dependent. The compounds employed in the present invention will exhibit unit cell volume expansion when compared to silicalite, but expansion is not limited to that derived from the data shown in Table I. It is believed that the above-mentioned unit cell expansion evidences the placement of magnesium as a part of the lattice framework structure. It is believed, without wishing to be bound by that belief, that altering the $SiO_2/MgO$ ratio varies the pore size and volume, framework density and refractive index of the resulting magnesium silicates. If small ranges of the $SiO_2/MgO$ ratios are utilized, the ability to detect volume, pore size and density differences will be dependent on the resolution capabilities of the analytical technique used.

Samples of compositions employed in the present invention whose crystallite size is appropriate to produce a distinct X-ray powder diffraction trace, have a pattern which includes at least the interplanar d spacings listed in Table II.

TABLE II

| Magnesium silicate, interplanar spacings d(Å) |
| --- |
| 11.2 ± 0.2 |
| 10.1 ± 0.2 |
| 10.0 ± 0.2 |
| 9.8 ± 0.2 |
| 6.0 ± 0.2 |
| 5.8 ± 0.2 |
| 5.6 ± 0.2 |
| 4.26 ± 0.1 |
| 3.85 ± 0.05 |
| 3.81 ± 0.05 |
| 3.74 ± 0.03 |
| 3.72 ± 0.03 |
| 3.64 ± 0.03 |

The range cited is due to unit cell volume expansion with decreasing $SiO_2/MgO$ ratio. Magnesium silicates with low Mg content in the $TO_4$ sites will be near the low d spacing limit and those with high Mg content in $TO_4$ sites will be near the high d spacing limit.

The compounds employed in the present invention are further characterized by a minimum of two reflections at 10.1±0.3 Å and a minimum of four reflections between 3.72 and 3.90 Å.

These values were obtained by Huber-Guinier techniques (preferred method) mentioned previously or by a Philips Electronics X-ray powder diffraction unit equipped with: scintillation-counter detector, graphite monochromator, and a strip chart recorder. The recorded reflections were identified by their two theta locations, after these locations were calibrated with an internal standard. The standard used was either NBS Si (NBS Circular 539, Vol. 9, p. 3) or $As_2O_3$. The magnesium silicate diffraction peaks at approximately 10.0 and 3.81 Å can often be obscured in poorly crystalline samples or in low-resolution X-ray diffraction data.

X-ray analyses of magnesium silicates of the present invention reveal distinct differences in the diffraction patterns as a result of specific treatments given to these magnesium silicates. Intensity changes are observed and lines may appear, disappear or merge depending on the exact calcination procedure utilized. Ion-exchange of these silicates may also cause changes in certain cases. Several authors have made similar observations on related materials like zeolite ZSM-5. See H. Nakamoto and H. Tarahashi, *Chem. Lett.*, 1013–1016 (1981). Regardless of the causes of the above-mentioned changes, they are expected by those people skilled in the art of analyzing porous crystalline silicates.

The magnesium silicates employed in this invention are characterized also by infrared analysis. The use of infrared analysis is recognized as a standard method in the characterization of inorganic and organic materials and has been used in the study of both natural and synthetic zeolites. See for example, E. M. Flanigen et al., *Adv. Chem. Series*, Vol. 101, p. 201–229, 1971. See also P. A. Jacobs, supra. For examples from the patent literature pertaining to the use of infrared analysis in zeolite characterization, see U.S. Pat. No. 4,257,885 to R. W. Grose and E. M. Flanigen and references included therein.

Figure 2:
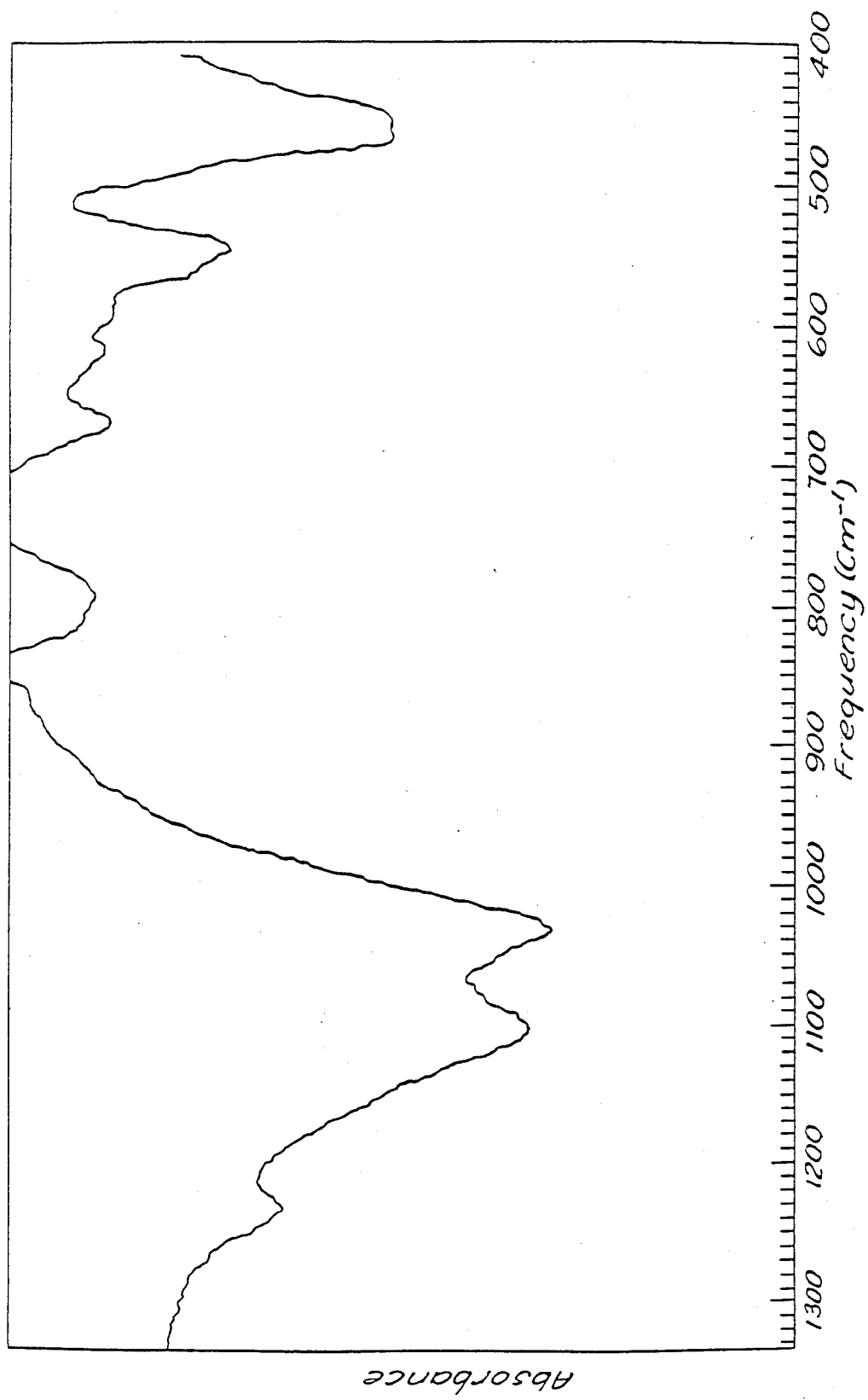
Figure 3:
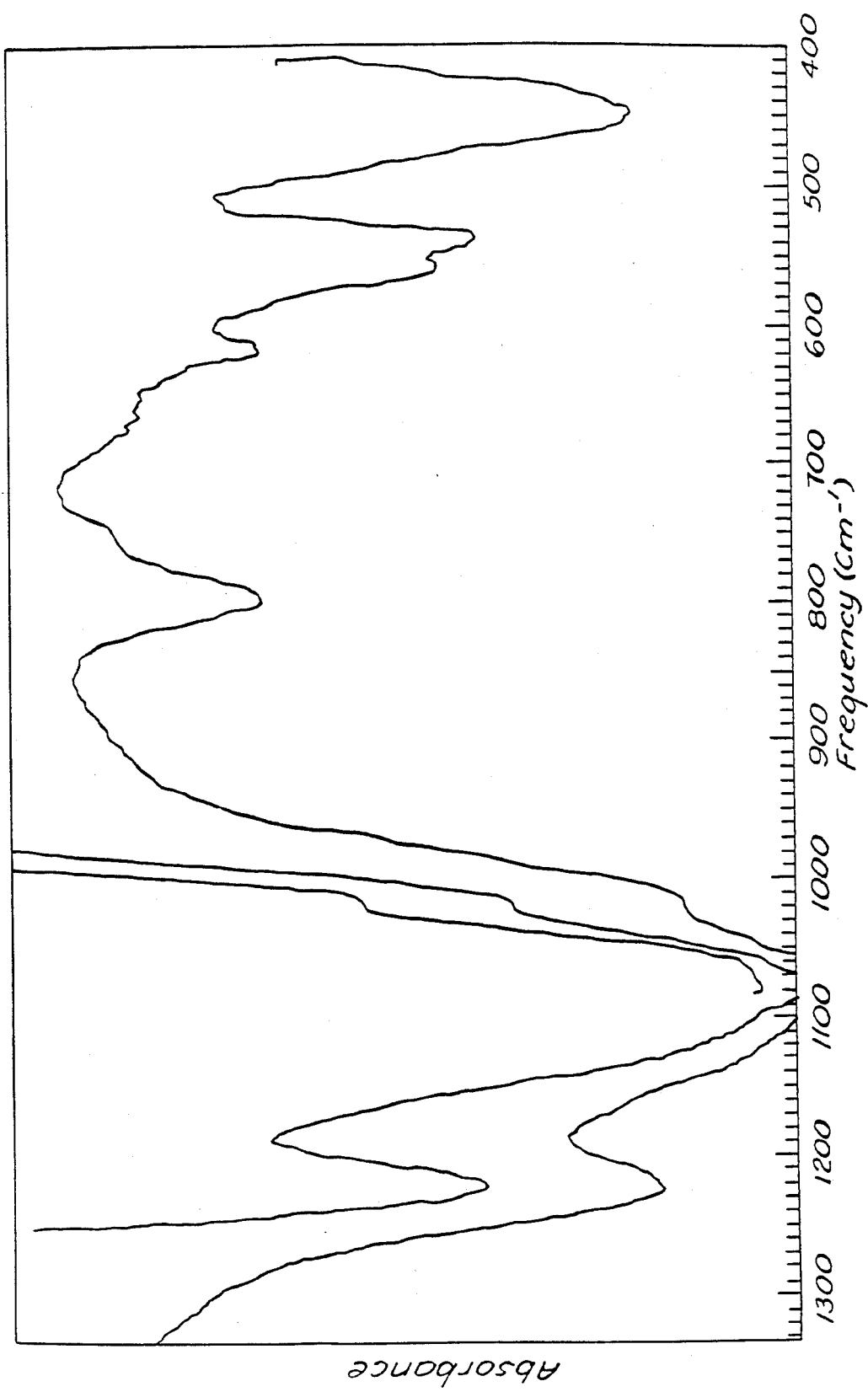

Magnesium silicates employed in the present invention exhibit unique features in the 1300-400 cm$^{-1}$ region. Many compositions exhibit at least two distinct bands in the 1200-980 cm$^{-1}$ region as shown in FIGS. 1, 2 and 3. Preferred compositions employed in the present invention exhibit these two distinct bands and also characteristic infrared bands at 1225±10 cm$^{-1}$, 800±20 cm$^{-1}$, 620±10 cm$^{-1}$, 550±20 cm$^{-1}$ and 450±20 cm$^{-1}$ as shown in FIGS. 1, 2 and 3.

Without wishing to be bound by any theory, it should be recognized that bands located between 1200-980 cm$^{-1}$ may be due to asymmetric stretch of TO$_4$ units in zeolites and silicates, see, e.g., Flanigen, et al. "Molecular Sieve Zeolites-1," *Adv. Chem. Series*, 101, 201 A.C.S. (1971). It is believed without being bound by that belief that the band found nearest to 980 cm$^{-1}$ in the present invention is due to silanol groups of the form —Si(OH)$_3$, >Si(OH)$_2$, ≡SiOH, or to their corresponding silicate forms.

Differential thermal analysis (DTA) is one of the thermal methods used in the literature as an aid in zeolite characterization. See D. W. Breck, *Zeolites Molecular Sieves*, John Wiley, 1974. See also European Patent Office Document 14,545 (Chu et al.), Jan. 24, 1980.

Compositions employed in the present invention may be analyzed by DTA methods. When using a du-Pont ®990 thermal analysis unit equipped with a 1200° C. furnace, a 10 mg sample is tested against alumina as a reference material (both contained in platinum crucibles). The heating rate for the system is 20° C. per minute in air with an air flow rate of 50 cc per minute. Under these conditions, one observes a distinct exotherm at 870°±30° C. X-ray diffraction (XRD) analysis of the sample both before and after the exotherm yields at least the interplanar d spacings listed in Table II, supra.

The compositions employed in this invention have ion-exchange properties. The ion-exchange capacity of traditional zeolites is associated with their aluminum content. The ion-exchange properties of the magnesium silicate employed in this invention are not necessarily dependent upon any one of its particular components. Indeed it is believed, without wishing to be bound to this belief, that the ion-exchange capacity of the compounds is due to a combination of factors. Among them are: the magnesium content, the trivalent metal ion content and also to the presence of internal silanol moieties within the silicate framework which under appropriate conditions can participate in the ion-exchange process.

Even though a relationship among the composition and the ion-exchange capacity of these solids is recognized, the present invention is not restricted by the traditional "linear relationship" between composition and ion-exchange capacity, characteristic of traditional zeolites.

The exchangeable cations in zeolite compositions often play a critical role in their synthesis by hydrothermal methods. In certain cases, a particular cation is required to obtain a given zeolite, for example, sodium is said to be required to produce zeolite X from aluminosilicate gels. Apparently the cation plays a template role in the formation of certain structures and/or acts as a crystallization promoter. The magnesium silicates employed in this invention do not appear to require a particular alkali metal cation for their formation. Crystalline compositions of the present invention are obtained from magnesium silicate gels in the presence of several alkaline metal salts including sodium or potassium salts. The presence of sodium or potassium ions during and/or after the synthesis may affect certain properties of the final product in applications which are susceptible to drastic changes by subtle differences such as catalysis and adsorption. Salts other than sodium and potassium may have similar effects.

In the synthesis of traditional zeolites the source of silica may be a critical factor in the preparation of certain zeolites. In the case of the present invention, the source of silica appears to have an effect in the morphology of the crystalline product. There are many examples in the literature relating morphology to a variety of useful properties of porous crystalline silicates like catalytic applications, ion-exchange, adsorption, etc.

Typically, the novel material is made by hydrothermal methods using one of many sources of silicon such as one of the commercially available soluble silicates or water glass solutions, amorphous silica, colloidal silica, silica gels, fumed silica or an organosilicate like (EtO)$_4$Si. Advantageously employed are two commercially available sources: a colloidal silica sold by the du Pont de Nemours Company under the trademark Ludox SM ® and a sodium silicate sold by the Philadelphia Quartz Company under the trademark Philadelphia Quartz Sodium Silicate N ®.

The source of magnesium usually is one of its water-soluble salts, magnesium chloride, acetate, sulfate, nitrate, etc., or a complex ion like Mg(NH$_3$)$_6^{2+}$, Mg(EDTA)$^{2-}$, etc., or a slightly soluble compound like Mg(OH)$_2$, MgF$_2$, etc. A magnesium chloride salt is a preferred source of magnesium.

Besides these components the reaction mixture will contain a solvent such as water, along with alkali metal ion salts such as, chlorides, sulfates or hydroxides of sodium, potassium, rubidium or cesium. The solvent may be added separately to the reaction mixture or may already be present with one of the reactants such as the silica source. Water is the preferred solvent.

A material which is believed, without wishing to be bound by that belief, to act as a crystallization promoter and is hereinafter termed a "crystallization promoter" is utilized in the process of making the porous crystalline magnesium silicate of the present invention. Typically, this crystallization promoter is (or is formed from) an organic nitrogen compound such as quaternary ammonium ion salts, or hexamethylene diamine, but may also be other compounds such as seed crystals typically of compositions similar to those crystals sought from the process. In particular, tetrapropyl ammonium ion salts are often used with tetrapropyl ammonium bromide and tetrapropyl ammonium hydroxide being preferred.

In a typical method of making these novel magnesium silicates, a magnesium source, a crystallization promoter, an alkali metal ion salt and a solvent are combined. The pH of this combination of chemicals is usually adjusted and the combination is further combined with a mixture of a silica source and a solvent to give a reaction mixture typically having a pH of about 11. The pH may advantageously be adjusted either above or below a pH of 11 to modify certain crystallization or process parameters such as the solubility of magnesium in the mixture, formation of precipitates, rates of crystallization, etc. The pH is adjusted as desired using acids or bases such as H$_2$SO$_4$ or NaOH and may be adjusted before, after and/or during the mixing step of the reactants.

The reaction mixture is vigorously mixed at room temperature for a sufficient time to produce an apparently homogeneous gel. Typically the rate of mixing is sufficiently vigorous to produce a satisfactory slurry or gel within one minute.

The mixture resulting from the above procedure is allowed to crystallize into compositions of the present invention. Preferably, crystallization takes place at temperatures above room temperature to increase the rate of crystal growth. Usually about 150° C. is used with autogeneous pressure. Higher or lower temperatures may be advantageously employed depending upon the process or product parameters desired, e.g., larger crystals are generally formed with lower temperatures and the rate of crystallization increases with higher temperatures. When quaternary ammonium ion salts are used as crystallization promoters, temperatures above 200° C. are avoided to prevent their decomposition.

Crystallization is allowed to proceed until crystals of the compositions employed in the present invention are formed. This may be determined by analysis of reaction mixture samples at intervals. The crystallization time will vary depending upon the reactants or the particular process parameters chosen. Crystallization times of one of five days are not uncommon.

During the crystallization step, stirring may be advantageously employed to facilitate product formation. The rate and type of stirring may affect crystallization parameters such as the rate of crystallization, uniformity of the product and crystal size. The effect of this parameter and optimum adjustment is dependent upon other parameters and is believed to be within the skill of the art to determine without undue experimentation.

Following crystallization it is often desirable to filter the crystallized mixture using a water wash to remove the mother liquor and then to heat the crystals to about 110° C. to remove water and thereby produce a convenient free-flowing powder.

The compositions as made by the above procedure may contain organic moieties which, if desired, may be removed by known methods such as calcination in an oxygen-containing atmosphere at a temperature sufficient to decompose the organic moieties. Calcination at about 500° C.–600° C. for approximately an hour is sufficient to remove commonly present organic moieties.

As mentioned before, the magnesium silicates employed in the invention may be beneficially modified by techniques well-known in the art which treat said silicates with acids, salts or other ions or molecules. Preparation of the acid form of the magnesium silicate is especially valued to produce a stable, catalytically active form of porous crystalline magnesium silicate for use in the present invention. As is known in the art, the acid form or hydrogen form of such compounds may be prepared by contacting with an ammonium salt solution followed by drying and calcining. Alternatively, the composition may be acid exchanged by contact with an acid solution such as hydrochloric acid.

As mentioned before, certain compositions employed in the invention may be expressed according to a formula in terms of the molar ratios of oxides on a dry basis, viz.,

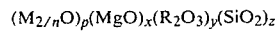
$(M_{2/n}O)_p(MgO)_x(R_2O_3)_y(SiO_2)_z$ wherein M is at least one ion-exchangeable cation having a valence of n; R is at least one element with valence 3+ which is not ion-exchangeable by conventional means; $x/z > 0$; $y/z \geq 0$; $p/n > y$; and p, x, z are positive numbers and y is a positive number or zero. The statement $x/z > 0$ is essential to all compositions employed in the present invention since it defines a magnesium silicate. All compositions employed in the present invention must contain magnesium.

The statement $y/z \geq 0$ indicates that this is a nonessential term. Typical nonion-exchangeable elements which may advantageously be present include by way of example, aluminum, iron, chromium, boron and gallium.

Also the above-mentioned formula could be modified to include other elements optionally present which are not ion-exchangeable by conventional means, including those having a valence other than 3+ such as 2+ or 4+. Germanium is an example of such an element. A preferred catalyst is also one that has been phosphorus treated in known manner to achieve selective isomer formation.

Preferred embodiments of magnesium silicates employed in the present invention expressed in terms of the above formula are those wherein p is from about 0.1 to about 20; x is from about 0.1 to about 12; y is from about 0 to about 3 and z is from about 84 to about 96. It is especially preferred that the term y of the above formula be from 0 to about 1.0.

Typically, the ion-exchangeable cations M (of both the magnesium silicates represented by the above formula and similar magnesium silicates suitably employed in the present invention) are alkali metals, hydrogen, group VIII metals or rare earth elements, or ammonium ions, but may be any element or moiety capable of exchange into the magnesium silicates employed in the present invention. As previously mentioned, it is preferred that at least some of the ion-exchangeable cations are hydrogen ions for use in the present invention. Methods of ion-exchange are well-known in the art, e.g., hydrogen may be exchanged into a silicate by simply treating with acid.

In the alkylation process, the aromatic compound to be alkylated is any aromatic compound containing at least one alkylatable ring position. Preferably, further substituents which would interfere with the alkylation by the formation of difficultly removable by-products or by deactivation of the catalyst whether due to tar formation or otherwise are absent. Most preferred aromatic compounds are benzene, toluene and ethylbenzene. One particularly unique advantage of the present process is the ability to alkylate a mixture of aromatic compounds, especially a mixture of benzene and toluene.

The alkylating agent is a convenient source of alkyl radicals. Suitable alkylating agents are α-olefins such as ethylene or propylene, lower alkyl halides or mercaptans such as ethyl or propyl chlorides or mercaptans and lower primary or secondary alcohols, especially methanol, ethanol or propanol. All alkylating agents previously known in the art may be employed in the present process. A preferred alkylating agent is ethylene.

Suitable temperatures are from about 300° C. to about 600° C. and preferably from about 350° C. to 500° C. Pressures from atmospheric to about 500 psig may be employed. Preferred are pressures from about 50 psig to 350 psig.

Optionally, modifying gases may be present in the reaction mixture. Suitably, hydrogen or an inert gas such as nitrogen, carbon dioxide or carbon monoxide may be present along with the reactants previously mentioned. The preferred modifying gas is hydrogen.

A further advantage of the present invention is that feed ratios of aromatic compound to alkylating agent may vary over wide extremes. On an equivalent basis, ratios from about 20/1 to about 1/1 are suitably employed. Preferred are ratios from about 10/1 to about 2/1.

The amount of catalyst employed is not critical to the success of the process since some amount of alkylated product is formed if suitable reaction times are provided. Advantageously, in a continuous process Where hydrogen is also present during the reaction, mole ratios of hydrogen/alkylating agent from about 10/1 to about 1/10 are suitably employed. Other diluent gases where employed may be present in about the same molar ratios.

An additional advantage of the present process is noted to be the almost total absence of disproportionation of alkylbenzenes when in contact with the present catalyst. For example, little or no formation of xylenes is observed when toluene is contacted with the catalyst under conditions of temperature and pressure suitably employed herein.

After prolonged use, particularly at extreme operating conditions, it may be desirable to regenerate the catalyst of the present process. The regeneration is performed in known manner, for example, by heating for several hours at a temperature of up to about 600° C. in the presence of steam, air or mixtures of air and nitrogen.

The above description and following examples are given to illustrate the invention, but these examples should not be taken as limiting the scope of the invention to the particular embodiments or parameters demonstrated since obvious modifications of these teachings will be apparent to those skilled in the art.

EXAMPLE 1

A solution A was made by combining 106 grams of commercially available Philadelphia Quartz Sodium Silicate N ® type (trademark of Philadelphia Quartz Company) (8.90 weight percent $Na_2O$, 28.7 weight percent $SiO_2$) with 132 grams of $H_2O$. A second solution B was made by combining 180 grams of $H_2O$, 40 grams of NaCl, 26 grams of $(C_3H_7)_4NBr$, 10.2 grams $MgCl_2.6H_2O$ and 8 grams of concentrated $H_2SO_4$ (96 weight percent) to form a clear solution.

Solution A was transferred to a Waring ® blender and the blender was started at the "high" setting. Solution B was added at once and the mixture was stirred vigorously for 1 minute. The resulting slurry was then placed inside a stainless steel autoclave, heated to about 150° C. under autogenous pressure and stirred. After 24 hours, the autoclave was cooled to room temperature and the solid product was isolated by filtration. The filter cake was washed several times with much water and then air dried at about 110° C. into a free flowing powder. X-ray powder diffraction (XRD) analysis of the powder gave a pattern similar to that reported for silicalite and ZSM-5.

EXAMPLE 2

A product made according to the procedure of Example 1 which is calcined overnight in air at about 500° C. to remove trapped organic matter produces changes in the relative intensities observed by XRD analysis.

Surface area measurements on a calcined solid, made according to the above procedure, by the single point BET method gave a measurement of 378 $m^2/g$.

Analysis of a product made according to the procedure in Example 1 by infrared spectroscopy using a Perkin-Elmer ® Model 337 double-beam instrument produces a characteristic spectrum with two distinct bands in the 1200–980 $cm^{-1}$ region.

Differential thermal analysis of a solid silicate (as made according to the procedure in Example 1) using a duPont ® 990 thermal analysis unit equipped with a 1200° C. furnace revealed a characteristic exotherm at about 860° C. The sample was heated at a rate of about 20° C./minute in a platinum crucible in an air atmosphere with an air flow rate of about 50 cc/minute. The product was recovered after heating to about 950° C. and was analyzed by XRD and found to contain all the lines listed in Table II.

EXAMPLE 3

The procedure of Example 1 was repeated but with a reaction temperature of 125° C. rather than 150° C. The solid dried at 110° C. was calcined at about 500° C. for 18 hours. Chemical analysis of the solid was done by neutron activation analysis and revealed on a molar ratio basis referred to $MgO:SiO_2$ (11.0), MgO (1.0), $Na_2O$ (0.38) and $Al_2O_3$ (0.015). The XRD analysis of the magnesium silicate product was consistent with the diffraction lines listed in Table II.

EXAMPLE 4

A reaction mixture was prepared as follows: (a) 100 g of commercially available Ludox SM ® (trademark of duPont) colloidal silica (30 weight percent $SiO_2$, 0.56 weight percent $Na_2O$) were mixed with 8.0 g of NaOH solution (50 weight percent NaOH) and 100 g of $H_2O$; (b) 26 g of $(C_3H_7)_4NBr$ were dissolved in 110 g of $H_2O$; (c) 10.2 g of $MgCl_2.6H_2O$ were dissolved in 100 g of $H_2O$.

The mixtures of (a) and (b) were mixed in a high torque blender for a few seconds and then solution (c) was added maintaining the mixing for about 1 minute to produce an apparently homogeneous mixture. The pH of the mixture was adjusted to about 11 by addition of NaOH (50 weight percent NaOH). The pH adjusted mixture was then transferred to a stainless steel autoclave and stirred at 150° C. for 30 hrs. under autogenous pressure. The product was recovered by filtration and rinsed with copious amounts of water. The lines observed by X-ray powder diffraction analysis of the solid match those values listed in Table II.

EXAMPLE 5

A porous crystalline magnesium silicate that was prepared substantially according to the process of Examples 1–4 was calcined overnight to remove organic moieties. This calcined material was then slurried with hot 1N $NH_4NO_3$ overnight. The material recovered by filtering this slurry was dried for several hours at about 110° C. Then one part of this magnesium silicate was mixed with one-half part kaolin clay and enough water to form a moist cake. The cake was dried and then calcined at about 500° C. in air for about 5 hours. This material was then crushed into 6–12 mesh aggregates.

About 9 g of the crushed aggregate was placed into the center portion of a ½×30″ 316 stainless steel reactor tube with 8-12 mesh silica on both sides acting as a support and aid to the uniform heating of the catalyst. A ⅛" thermowell inside the reactor was equipped with a thermocouple for measuring reactor temperatures. The reactor was placed inside an electric furnace and heated to about 370° C. A hydrogen gas feed was begun and the pressure increased to about 100 psig and then toluene was fed to the reactor. When toluene was detected downstream from the reactor, the ethylene feed was started.

The toluene was pumped into the reactor at a rate of about 121 g per hour, hydrogen gas was added at a rate of about 240 cc per minute as measured at ambient pressure and temperature, and ethylene was added at a rate of about 75 cc per minute as measured at about 21° C. and about 760 mm Hg pressure. The reactor was operated at about 100 psig with a negligible pressure drop across the catalyst bed.

About 3½ hours after the ethylene feed stream was turned on, a sample of the reactor effluent was taken and analyzed by conventional gas chromatographic methods. The results are given in Table III below.

TABLE III

| Reactor Effluent Analysis | Mole Percentage in Liquid Effluent |
|---|---|
| Benzene | 0.03 |
| Toluene | 88.15 |
| EBX* | 0.126 |
| para-Ethyltoluene | 7.83 |
| ortho-Ethyltoluene | — |
| meta-Ethyltoluene | 3.55 |
| DEB** | 0.15 |

*Ethylbenzene and xylenes.
**Diethylbenzene.

The molar feed ratios for the above process were approximately 7 to 1 to 3 for toluene to ethylene to hydrogen. The above analysis gives approximately an 80.1 percent conversion rate to ethyltoluene for ethylene based upon a maximum theoretical conversion calculated by dividing the mole per hour feed rate for ethylene by that for toluene.

EXAMPLE 6

The reaction conditions of Example 5 were substantially repeated employing varying temperatures, pressures and amounts of hydrogen, ethylene, aromatic compound and nitrogen identified in Table IV. Except where noted, analysis of the reactor effluent by gas/liquid chromatograph was made after 24 hours of continuous operation at reaction conditions. The catalyst was 8.0 grams of supported catalyst prepared according to the procedure of Example 5. In the table, ET is ethyltoluene, p-ET is para-ethyltoluene, m-ET is meta-ethyltoluene, and o-ET is ortho-ethyltoluene.

TABLE IV

| Run | °C. | psig | $H_2$ (mole/hr) | $C_2H_4$ (mole/hr) | toluene (mole/hr) | $N_2$ (mole/hr) | $C_2H_4$ Conv. | % p-ET | % m-ET | % o-ET | % ET Sel. | Note |
|---|---|---|---|---|---|---|---|---|---|---|---|---|
| 1 | 380 | 100 | 0.45 | 0.15 | 1.06 | 0 | 69 | 54.0 | 45.4 | 0.6 | 96 | a |
| 2 | 380 | 100 | 0.45 | 0.07 | 0.46 | 0 | 78 | 44.6 | 54.7 | 0.7 | 97 | a |
| 3 | 380 | 200 | 0.53 | 0.07 | 0.46 | 0 | 89 | 41.3 | 57.9 | 0.8 | 96 | a |
| 4 | 460 | 35 | 0.09 | 0.30 | 2.06 | 0 | 48 | 52.8 | 46.3 | 0.9 | 97 | a |
| 5 | 480 | 200 | 0.14 | 0.30 | 2.06 | 0 | 89 | 36.1 | 62.2 | 1.7 | 96 | a,b |
| 6 | 385 | 100 | 0 | 0.15 | 1.08 | 0.06 | 74 | 51.2 | 48.0 | 0.8 | 94 | c |
| 7 | 408 | 280 | 0.45 | 0.25 | 1.05 | 0 | 79 | 43.0 | 55.8 | 1.2 | 95 | d |

<sup>a</sup>Conversion was essentially constant during 24 hours.
<sup>b</sup>Air regeneration between runs 4 and 5.
<sup>c</sup>Air regeneration between runs 5 and 6, results after 2 hours operation.
<sup>d</sup>Air regeneration between runs 6 and 7, results after 4 hours operation.

EXAMPLE 7

The reaction conditions of Example 5 were substantially repeated excepting that the aromatic reactant was benzene. Accordingly, 8.0 grams of catalyst prepared substantially according to the methods of Example 5 was employed. The process conditions and results upon analysis of the reactor effluent after 18 hours of operation at 415° C. and 100 psig are contained in Table V.

TABLE V

| $H_2$ (mole/hr) | $C_2H_4$ (mole/hr) | Benzene (mole/hr) | $C_2H_4$ % Conv. | EB % Sel. |
|---|---|---|---|---|
| 0.55 | 0.42 | 1.27 | 90 | 70 |

EXAMPLE 8

The reaction conditions of Example 5 were substantially repeated excepting that the alkylating agent employed was methanol. Accordingly, 20.0 grams of bound catalyst pellets prepared substantially according to the method of Example 5 were employed. The results obtained by analysis of effluent after 24 hours of continuous operation are contained in Table VI. The reaction conditions are as follows: Temperature—379° C., Pressure—25 psig, feed rates: toluene—1.02 mole/hr, methanol—0.15 mole/hr, hydrogen—0.16 mole/hr.

TABLE VI

| Methanol % Conv. | Xylene % Selectivity | Xylene distribution | | |
|---|---|---|---|---|
| | | ortho- | meta- | para- |
| 79 | 73 | 29.4 | 35.2 | 35.4 |

EXAMPLE 9

The reaction conditions of Example 5 were again substantially repeated excepting that the aromatic compound was a mixture of benzene and toluene. Accordingly, about 8.0 grams of magnesium silicate catalyst prepared substantially according to the procedure of Example 5 were employed. The following conditions were employed: reactor temperature—422° C., pressure—100 psig, $C_2H_4$ feed rate—170 cc/min measured at ambient temperature and pressure, $H_2$ feed rate—78 cc/min measured at ambient temperature and pressure. An aromatic feed of benzene and toluene in a molar ratio of 89/11 was supplied to the reactor at a rate of 99.2 g/hr.

After 2 hours continuous operation at the above reaction conditions, the reactor effluent was analyzed by gas-liquid chromatography. Results are contained in Table VII.

TABLE VII

| Component | Mole % |
|---|---|
| benzene | 64.03 |
| toluene | 8.92 |
| ethylbenzene | 19.36 |
| p-ethyltoluene | 1.44 |
| m-ethyltoluene | 1.94 |
| o-ethyltoluene | 0.07 |
| p-diethylbenzene | 1.92 |
| m-diethylbenzene | 2.18 |
| o-diethylbenzene | 0.03 |

Benzene conversion was 27.9 percent. Toluene conversion was 20.0 percent. Ethylene conversion was 91.6 percent. The process is seen to be particularly advantageous in that xylene formation due to disproportionation of toluene is extremely low. Because ethylbenzene and xylenes are extremely difficult to separate by fractional distillation, the present process for alkylating a mixture of benzene and toluene is highly advantageous due to the near lack of xylene formation.

What is claimed is:

1. A process for alkylating an aromatic hydrocarbon comprising contacting an alkylating agent with an aromatic hydrocarbon under reactive conditions in the presence of a catalytic amount of a porous crystalline magnesium silicate.

2. A process according to claim 1 wherein the porous crystalline magnesium silicate corresponds to the following formula in terms of the molar ratios of oxide on a dry basis:

$$(M_{2/n}O)_p(MgO)_x(R_2O_3)_y(SiO_2)_z$$

wherein M is at least one cation having a valence n; R is a trivalent element or mixture thereof; x/z>0; y/z≧0; p/n>y; and p, x, z are positive numbers and y is a positive number or zero, further characterized by an X-ray diffraction trace having at least those interplanar d spacings listed in Table II of the specification.

3. A process according to claim 2 wherein p is from about 0.1 to about 20; x is from about 0.1 to about 12; y is from about 0 to about 3 and z is from about 84 to about 96.

4. A process according to claim 3 wherein y is from zero to about 1.0.

5. A process according to claim 2 wherein M is hydrogen.

6. A process according to claim 2 wherein R is at least one of chromium, iron, aluminum, boron or a mixture thereof.

7. A process according to claim 2 wherein the crystalline magnesium silicate is in the hydrogen form.

8. A process according to claim 2 wherein the porous crystalline magnesium silicate is further characterized by infrared analysis in that said analysis reveals at least two distinct bands in the 1200–980 cm$^{-1}$ region.

9. A process according to claim 8 wherein the porous crystalline magnesium silicate is further characterized by infrared analysis in that said analysis reveals at least one or more additional bands at 1225±10 cm$^{-1}$, 800±20 cm$^{-1}$, 620±10 cm$^{-1}$, 550±20 cm$^{-1}$ and 450±20 cm$^{-1}$.

10. A process according to claim 8 wherein said distinct infrared analysis bands are present both before and after calcination at about 500° C.–700° C.

11. A process according to claim 2 wherein said silicate when subjected to differential thermal analysis using alumina as a reference and a heating rate of about 20° C. per minute in an air atmosphere at an air flow rate of about 50 cc per minute reveals a distinct exotherm at 870±30° C.

12. A process according to claim 10 wherein said silicate when subjected to differential thermal analysis in an air atmosphere using alumina as a reference and at a heating rate of about 20° C. per minute and with an air flow rate of about 50 cc per minute reveals a distinct exotherm at 870±30° C.

13. A process according to claim 11 wherein the porous crystalline magnesium silicate is further characterized by having at least those X-ray diffraction lines given in Table II of the specification both before and after said exotherm at 870±30° C.

14. A process according to claim 12 wherein the porous crystalline magnesium silicate is further characterized by having at least those X-ray diffraction lines given in Table II of the specification both before and after said exotherm at 870±30° C.

15. A process according to claim 2 wherein the porous crystalline magnesium silicate corresponds to the following formula in terms of the molar ratios of oxides on a dry basis:

$$(Na_2O)_p(MgO)_x(SiO_2)_z$$

wherein x/z>0; x<z and p, x and z are positive numbers; and is further characterized by infrared analysis in that said analysis reveals two distinct bands in the 1200–980 cm$^{-1}$ region.

16. A process according to claim 15 wherein p is from about 0.1 to about 20; x is from about 0.1 to about 12; and z is from 84 to about 96.

17. A process according to claim 1 wherein the aromatic hydrocarbon is toluene.

18. A process according to claim 1 wherein the alkylating agent is an α-olefin, a lower alkyl halide or mercaptan, or a lower primary or secondary alcohol.

19. A process according to claim 18 wherein the alkylating agent is ethylene, propylene, ethyl chloride, propyl chloride, ethyl mercaptan, propyl mercaptan, methanol, ethanol or propanol.

20. A process according to claim 1 wherein the ratio of aromatic hydrocarbon to alkylating agent is from about 20/1 to about 1/1.

21. A process according to claim 20 wherein the ratio of aromatic hydrocarbon to alkylating agent is from about 10/1 to about 2/1.

22. A process according to claim 1 wherein the temperature is from about 300° C. to about 600° C.

23. A process according to claim 22 wherein the temperature is from about 350° C. to about 500° C.

24. A process according to claim 1 wherein the pressure is from about atmospheric to about 500 psig.

25. A process according to claim 24 wherein the pressure is from about 50 psig to about 350 psig.

26. A process according to claim 1 wherein hydrogen gas is additionally present in the reaction mixture.

27. A continuous process according to claim 1 wherein the reactants and catalyst are contacted in a weight hourly space velocity based on aromatic compound of from about 0.1 to about 50.

* * * * *